(12) United States Patent
Weiger

(10) Patent No.: US 9,709,794 B2
(45) Date of Patent: Jul. 18, 2017

(54) ENDOSCOPE WITH ADJUSTABLE VIEWING ANGLE

(75) Inventor: Ulrich Weiger, Rangendingen (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 494 days.

(21) Appl. No.: 13/198,450

(22) Filed: Aug. 4, 2011

(65) Prior Publication Data

US 2012/0035421 A1 Feb. 9, 2012

(30) Foreign Application Priority Data

Aug. 4, 2010 (DE) .................. 10 2010 033 423

(51) Int. Cl.
| | | |
|---|---|---|
| A61B 1/06 | (2006.01) | |
| A61B 1/00 | (2006.01) | |
| G02B 23/24 | (2006.01) | |
| G02B 19/00 | (2006.01) | |
| A61B 1/04 | (2006.01) | |
| A61B 5/00 | (2006.01) | |

(52) U.S. Cl.
CPC ..... *G02B 23/2423* (2013.01); *G02B 19/0023* (2013.01); *G02B 19/0028* (2013.01); *G02B 19/0061* (2013.01); *A61B 1/00096* (2013.01); *A61B 1/00177* (2013.01); *A61B 1/00186* (2013.01); *A61B 1/041* (2013.01); *A61B 1/042* (2013.01); *A61B 1/043* (2013.01); *A61B 1/0607* (2013.01); *A61B 1/0676* (2013.01); *A61B 1/0684* (2013.01); *A61B 5/0066* (2013.01)

(58) Field of Classification Search
CPC ..... A61B 5/0084; A61B 1/043; A61B 5/0071; A61B 1/041; A61B 5/0066; A61B 1/00177; A61B 1/00186; A61B 1/042; A61B 1/0676; A61B 1/0684; A61B 1/00096; A61B 1/0607; A61B 1/0615; A61B 1/0661; A61B 1/07; A61B 1/227
USPC ..... 600/74–75, 103, 109, 170, 173, 38, 160, 600/177
See application file for complete search history.

(56) References Cited

U.S. PATENT DOCUMENTS 6,464,633 B1 * 10/2002 Hosoda et al. ............ 600/178
6,560,013 B1 * 5/2003 Ramsbottom ............. 359/431
(Continued)

FOREIGN PATENT DOCUMENTS

| DE | 60015375 T2 | 2/2006 |
|---|---|---|
| WO | 2010080991 A2 | 7/2010 |

OTHER PUBLICATIONS

German Search Report; Application No. 10 2010 033 423.5; Issued: Mar. 31, 2011; 4 pages.

*Primary Examiner* — John P Leubecker
*Assistant Examiner* — Rajaa El Alami
(74) *Attorney, Agent, or Firm* — Whitmyer IP Group LLC

(57) ABSTRACT

An endoscope with adjustable viewing angle, in which the viewing angle can pivot around a pivot axis, includes a fixed reflecting surface for reflecting illuminating light from a direction parallel to the longitudinal axis of the endoscope to a direction parallel to the pivot axis of the viewing angle and a pivotable reflecting surface for reflecting illuminating light from a direction parallel to the pivot axis of the viewing angle to the viewing angle for illuminating an object observed by the endoscope, such that at least either the fixed reflecting surface or the pivotable reflecting surface is curved.

9 Claims, 3 Drawing Sheets

(56) References Cited

U.S. PATENT DOCUMENTS 7,631,989 B2 * 12/2009 Li .................................. 362/298
2006/0256450 A1    11/2006 Tesar et al.

* cited by examiner

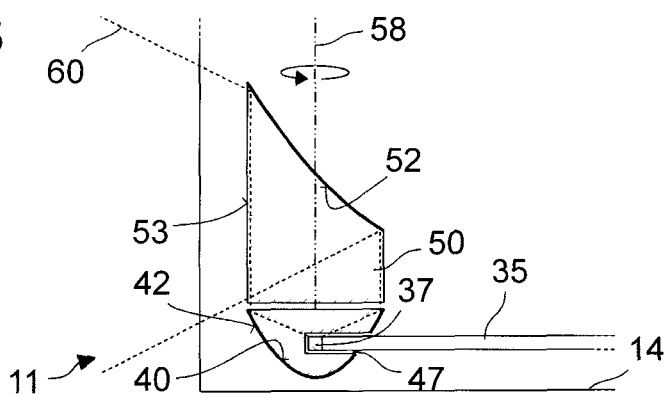
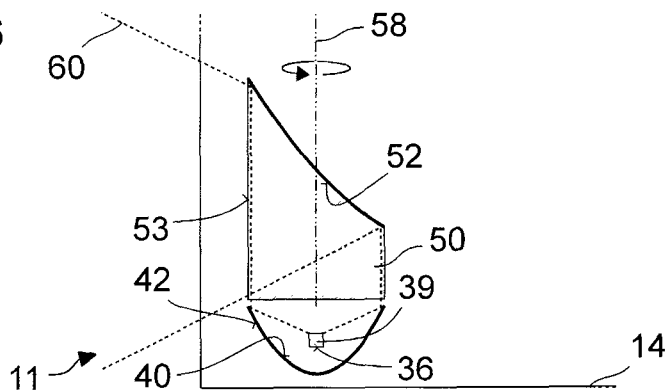

ENDOSCOPE WITH ADJUSTABLE VIEWING ANGLE

CROSS-REFERENCE TO RELATED APPLICATIONS

The present application claims priority of German patent application No. 10 2010 033 423.5 filed on Aug. 4, 2010, the content of which is incorporated herein by reference.

FIELD OF THE INVENTION

The present invention relates to an endoscope with adjustable viewing angle and to a method for illuminating an adjustable visual field.

BACKGROUND OF THE INVENTION

In addition to endoscopes with medical and non-medical technical applications whose viewing angle is parallel to the longitudinal axis of the endoscope shaft, endoscopes with other fixed viewing angles were developed for some time in the past. The viewing angle of an endoscope is understood here and hereinafter always to refer to the angle looking from the distal end of the endoscope, in which an object lies that appears in the center of the image recorded in each case by the endoscope. In many applications, however, a fixed viewing angle is a disadvantage. In the most unfavorable case, for example, the endoscope must be replaced repeatedly during a medical procedure. In such cases the use of an endoscope with an adjustable or displaceable viewing angle in situ is advantageous.

Observation of an object in a cavity by means of an endoscope, as a rule, requires the object to be illuminated. For this purpose an endoscope comprises, for example, lightwave conductors, in particular glass fibers, by means of which illuminating light is transmitted from the proximal end of the endoscope along the shaft to the distal end of the endoscope. Light outlet surfaces of the lightwave conductors on the distal end of the endoscope are positioned and configured in such a way that the entire visual field or viewing field is sufficiently illuminated.

In an endoscope with adjustable viewing angle, the illuminating light on the distal end of the endoscope is distributed, in the simplest case, in such a way that, depending on the particular viewing angle selected, the entire visual field is illuminated. This leads to a series of disadvantages, however. In particular, light capacity is wasted because the entire viewing fields of all adjustable viewing angles are constantly illuminated, independently of the viewing angle actually selected. At a predetermined desired brightness, a markedly higher light capacity must thus be made available than with an endoscope with fixed viewing angle.

An additional disadvantage is that illuminating light of higher intensity can photothermally or photochemically harm tissue or other objects. With an endoscope of fixed viewing angle, as a rule too little distance occurs from the distal end of the endoscope to an object, at least in observing the recorded image. In using a video camera on the endoscope, an automatic warning of users is also possible when the brightness of a recorded image exceeds a predetermined threshold. In an endoscope with adjustable viewing angle, however, part of the illuminating light impinges on objects situated outside the visual field. Therefore undesired approach of the distal end of the endoscope to these objects and a resulting radiation of these objects with too high a radiant capacity are avoided.

A further disadvantage consists in the fact that illuminating light that is at first radiated outside the visual field can be scattered or reflected by objects or opaque media. Reflected or scattered illuminating light can reach the observation beam path directly or indirectly. Consequently, contrasts and especially in dark image areas the distinguishability of objects can be reduced. In addition, visible, disturbing reflections can thereby be generated.

An additional disadvantage comes from the fact that the illumination strength, or intensity, of the illuminating light is essentially constant in the direction in which the viewing angle can be varied (often referred to also as the vertical direction), while in the direction perpendicular thereto (often called the horizontal direction) as a rule it slightly declines toward the edge of the visual field. From endoscopes with fixed viewing angle, however, users are as a rule accustomed to an illumination strength that slightly declines toward the edge of the visual field both in the horizontal and in the vertical direction. Therefore the illumination strength that is constant in the vertical direction can be experienced as an irritation.

Patent DE 600 15 375 T2 describes an arrangement of two prisms. One of said prisms can rotate around an axis to cast illuminating light at an adjustable viewing angle. The inventors of the present invention, however, have determined that the distribution of the illuminating light inside the visual field with the described arrangement of prisms is unsatisfactory in many cases. This distribution is determined by the light source or the fiber bundle and cannot be influenced by the prisms.

SUMMARY OF THE INVENTION

It is an object of the present invention to provide an improved endoscope with adjustable viewing angle and an improved method for illuminating an adjustable visual field.

Said object is achieved by the content of the independent claims.

Refinements are indicated in the dependent claims.

Embodiments of the present invention are based on the idea of providing a curvature or dome to at least either a fixed reflecting surface or a pivotable reflecting surface for directing illuminating light to an adjustable viewing angle. As a result of the curvature of the fixed reflecting surface and/or of the pivotable reflecting surface, a beam formation or a free configuration of the illuminating light bundle within certain boundaries is possible. Individual configuring possibilities are described hereinafter.

An endoscope with an adjustable viewing angle in which the viewing angle can be pivoted around a pivot axis includes a fixed reflecting surface for reflecting illuminating light from a direction parallel to the longitudinal axis of the endoscope to a direction parallel to the pivot axis of the viewing angle and a pivotable reflecting surface for reflecting observation light from a direction parallel to the pivot axis of the viewing angle to the viewing angle for illuminating an object observed by the endoscope, such that at least either the fixed reflecting surface or the pivotable reflecting surface is curved.

The illuminating light is present at almost every site as a divergent or convergent light bundle. The direction of the illuminating light in each case is understood to mean the center direction of the illuminating light inside the light bundle present at the particular location. If the illuminating light is present as a rotationally symmetrical light bundle, the direction of the illuminating light is the direction of the axis of symmetry. If the illuminating light is present as a light bundle with, for example, an elliptical cross-section with two planes of symmetry, the direction of the illuminating light is the direction of the intersection lines of the two planes of symmetry. The illuminating light in particular is directed in such a way that the direction of the illuminating light in some cases corresponds to the direction of the optical axis of the optical elements by which the illuminating light is directed.

The longitudinal axis of the endoscope is in particular the longitudinal axis of the shaft. In the case of a rigid, straight shaft, the longitudinal axis of the shaft is the straight line on which the center points of the cross-section surfaces of the shaft are situated. In the case of a flexible shaft, the longitudinal axis of the endoscope is the longitudinal axis of the distal end of the shaft, that is, the straight line on which the center points of the cross-section surfaces of the shaft close to its distal end are situated. The pivot axis is in particular perpendicular to the longitudinal axis of the endoscope.

The pivotable reflecting surface, in particular, can pivot around a pivot axis, which is parallel to the pivot axis of the viewing angle or identical with it.

A curved reflecting surface can comprise a continuous curvature, in particular a curvature that is constant along a sectional line with a plane or is a continuous function or smooth function of the location. Examples are spherical, torical (various curvatures or curvature radii in two planes of intersection perpendicular to one another), elliptical, hyperbolic forms. Alternatively a curved reflecting surface comprises for example several flat portions that can border directly on one another.

Owing to the curvature, the fixed reflecting surface and/or the pivotable reflecting surface does not simply act to divert the illuminating light. Instead, a curved reflecting surface can simultaneously have the effect of imaging or of forming the light bundle of the illuminating light. Because of the integration of the effect of diverting the illuminating light and forming the illuminating light bundle in the same two reflecting surfaces, it is possible to limit not only the number of optical elements but also, as a result, the production costs.

Forming the illuminating light bundle by the fixed and/or pivotable reflecting surface makes possible, in addition, an intervention precisely at the site at which it is constructively advantageous, if the illuminating light bundle comprises a minimal cross-section. The curvature of the fixed reflecting surface and/or the curvature of the pivotable reflecting surface can thus contribute to transmitting an especially high radiance from the reflecting surfaces and directing it to the adjustable viewing angle.

In an endoscope as described here, the fixed reflecting surface can be configured and positioned in order to collimate illuminating light.

On the basis of the collimating effect of the fixed reflecting surface, illuminating light is directed downstream in the light path from the fixed reflecting surface, in particular parallel or essentially parallel.

The parallel alignment of the illuminating light, in particular parallel to the pivot axis of the viewing angle, facilitates a diversion of the illuminating light into a momentarily selected viewing angle by the pivotable reflecting surface. Faulty adjustment of the pivotable reflecting surface, given parallelism of the illuminating light falling on the pivotable reflecting surface, can have a lesser impact than with a convergent or divergent light bundle.

In an endoscope as described here, the fixed reflecting surface can have the shape of a segment of a paraboloid.

In particular, the fixed reflecting surface has the shape of a segment of a paraboloid that is rotation-symmetrical to an axis of symmetry. The axis of symmetry of the rotation-symmetrical paraboloid, in particular, is parallel to the pivot axis of the viewing angle. In particular, this configuration and positioning of the fixed reflecting surface make possible a collimation of light that is emitted from a light outlet surface positioned at the focal point of the paraboloid.

Unlike, for example, collimation by means of a lens that could be positioned upstream in the light path or else downstream in the light path from a flat fixed reflecting surface, the paraboloid fixed reflecting surface makes it possible to dispense with a component (namely the lens), reduce adjustment expense and have a more compact structure.

In particular, a light outlet surface of a lightwave conductor or of a light source is positioned at a focal point of the paraboloid.

Positioning a light outlet surface of a lightwave conductor or of a light source at the focal point of the parabolically shaped fixed reflecting surface causes a collimation of the illuminating light emanating from the light outlet surface. In particular, in positioning the axis of symmetry of the paraboloid parallel to the pivot axis of the viewing angle, the illuminating light is directed downstream in the light path from the reflecting surface parallel to the pivot axis of the viewing angle. The illuminating light bundle can be to a great extent freely shaped by means of the pivotable reflecting surface positioned downstream in the light path. Owing to the parallel alignment of the illuminating light between the paraboloid, fixed reflecting surface and the pivotable reflecting surface, the illumination of a visual field can be largely or completely independent of the viewing angle in which the visual field is situated.

In an endoscope as described here, the pivotable reflecting surface can have the shape of a segment of a paraboloid or can be of torical shape.

The paraboloid, in particular, is a rotation paraboloid (that is, rotation-symmetrical to an axis of symmetry) or other elliptical or hyperbolic paraboloid. A torical surface has different curvature radii in two sectional planes that are perpendicular to one another.

In an endoscope as described here, the curvature of the pivotable reflecting surface can be adapted to the aspect ratio of the visual field that is to be illuminated.

In particular, with illuminating light collimated, as described above, between the fixed reflecting surface and the pivotable reflecting surface, it is possible, by means of a pivotable reflecting surface with the shape of a segment of a rotation paraboloid, to generate an intensity of the illuminating light that is rotation-symmetrical to the viewing angle downstream in the light path from the pivotable reflecting surface. This is experienced as familiar and pleasant by medical personnel, in particular in direct observation through the eyepiece or with use of a video camera that records an image with the aspect ratio 1:1. Also with an image with the aspect ratio 4:3, it is possible in some cases still to use an intensity of the illuminating light that is rotation-symmetrical to the viewing angle.

However, this is a clear trend toward use of HD video cameras with a resolution of 1920×1200 pixels or of 1920×1080 pixels and a corresponding aspect ratio of 16:10 or 16:9. With such an aspect ratio, an intensity of the illuminating light that is rotation-symmetrical to the viewing angle can be experienced by medical personnel as unaccustomed or irritating. In particular in the collimation of the illuminating light between the fixed reflecting surface and the pivotable reflecting surface, as described above, the distribution of the illuminating light in the visual field can be adapted to the aspect ratio of the visual field.

For this purpose the pivotable reflecting surface has, in particular, the shape of a non-rotation-symmetrical elliptical paraboloid or of a hyperbolic paraboloid or a torical shape, such that the axes or curvature radii are adjusted to the size of the visual field or to its aspect ratio. Adjustment here means in particular that the illuminated surface corresponds to the visual field, and/or that, for a surface that is flat (for example, essentially rectilinear or essentially elliptical) and perpendicular to the viewing angle within which the intensity of the illuminating light has a minimum value (in particular half of the maximum intensity), the ratio between width and height corresponds to the ratio between width and height of the visual field.

In an endoscope as described here, at least either the fixed reflecting surface or the pivotable reflecting surface can be positioned on a transparent body.

A transparent body, into which light enters through a light inlet surface and from which light exits through a light outlet surface and in which the light between the light inlet surface and the light outlet surface is reflected on a reflecting surface, is often referred to as a prism. The reflecting effect of the reflecting surface can be based on total reflection on a reflecting coating. In an endoscope as described here, the fixed reflecting surface and/or the pivotable reflecting surface can each be positioned on a transparent body whose shape is clearly distinguished from a prism in the narrower geometric sense. In particular, at least either the fixed reflecting surface or the pivotable reflecting surface is curved or domed. The light inlet surface and light outlet surface of a transparent body can also each be domed in concave or convex manner.

In particular, reflection of light on the basis of total reflection on a reflecting surface of the transparent body has the advantage of especially high, in fact maximum, reflectance. Many transparent types of glass can be processed well and precisely. Production of a reflecting surface on a transparent body of glass can therefore simultaneously allow especially good optical properties and cost-efficient manufacturing.

In an endoscope as described here, the fixed reflecting surface can be positioned on a transparent body, such that the transparent body and a light outlet surface of a lightwave conductor or light source are joined by means of a transparent cement.

The light source is, for example, a light-emitting diode, a body that can be excited to fluorescence by means of laser light or that is otherwise luminescent. The light outlet surface can include a plane, in particular a circular or polygonal or concave or convex shape, and thereby can include several flat polygonal partial surfaces. By joining the light outlet surface to the transparent body by means of a transparent cement, it is possible to reduce, or largely or completely to prevent, the loss of radiant power of the illuminating light by reflection on bordering surfaces. The light outlet surface can be positioned in a borehole in the transparent body, in particular on the base or ground or end of a blind hole.

In an endoscope as described here, the pivotable reflecting surface and the fixed reflecting surface can be configured and positioned in such a way that a light bundle of illuminating light emerging on the distal end of the endoscope includes a tapering downstream in the light path from the pivotable reflecting surface.

A tapering downstream in the light path from the pivotable reflecting surface can reduce the need for space for the illuminating beam path on the distal end of the endoscope. In particular, the required size of a window component through which the illuminating light exits on the distal end of the endoscope can thereby be reduced.

In a method for illuminating a visual field in a viewing angle of an endoscope, such that the viewing angle of the endoscope can pivot around a pivot axis, illuminating light is provided and the provided illuminating light is diverted first in a direction parallel to the pivot axis by means of a fixed reflecting surface and then diverted to the momentarily selected viewing angle by means of a pivotable reflecting surface, such that the spatial area illuminated by the illuminating light is adjusted to the visual field upon diverting at least either by means of a curvature of the fixed reflecting surface or by a curvature of the pivotable reflecting surface.

A method for illuminating a visual field as described here can be performed in particular by means of an endoscope as described here.

BRIEF DESCRIPTION OF THE DRAWINGS

Hereinafter, embodiments are described more closely with reference to the appended drawings, which are as follows:

FIG. 5 shows a schematic depiction of a distal end of an additional endoscope with adjustable viewing angle.

FIG. 6 shows a schematic depiction of a distal end of an additional endoscope with adjustable viewing angle.

DETAILED DESCRIPTION OF THE INVENTION

Figure 1:
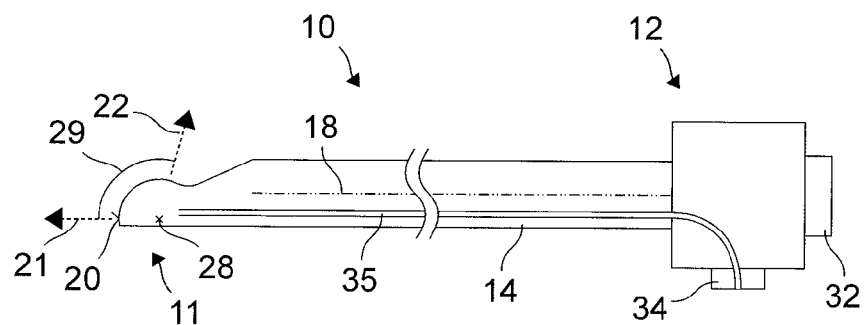
FIG. 1 shows a schematic depiction of an endoscope with adjustable viewing angle.

FIG. 1 shows a schematic depiction of an endoscope 10 with a distal end 11, a proximal end 12 and a rigid shaft that extends from the distal end 11 to the proximal end 12. Alternatively, the shaft 14 is flexible or partially flexible. The cross-section of the shaft 14 or at least the outer contour of the cross-section of the shaft 14 is constant or essentially constant between the distal end 11 and the proximal end 12. In particular, the contour of the cross-section of the shaft 14 is circular or elliptical. In this case the longitudinal axis 18 of the endoscope 10 shown in FIG. 1 is the axis of symmetry of the mantle surface of the shaft 14 between the distal end 12 and the proximal end 11. In a cylindrical mantle surface of the shaft 14, the longitudinal axis 18 is also the aggregate of the center points or surface centers of gravity of the cross-sections of the shaft 14 between the distal end 12 and the proximal end 11. In a circular-cylindrical mantle surface 14, the longitudinal axis 18 is also the axis of symmetry of the mantle surface.

On the distal end 12, the shape of the shaft 14 departs from cylindrical symmetry, as is shown by way of example in FIG. 1. In particular, the shaft 14 comprises on its distal end 12 an aperture that is closed by a transparent window component with a domed surface 20. In particular, the window component with domed surface 20 closes the aperture with a hermetic insulation. The surface 20 of the window component has, for example, the shape of a segment of a circular-cylindrical mantle, so that the axis of symmetry of the circular cylinder is perpendicular to the longitudinal axis 18 of the endoscope 10 and to the plane of projection of FIG. 1. Alternatively, the surface 20 of the transparent window component has the shape of a section of a spherical surface or of a rotation-symmetrical or non-rotation-symmetrical ellipsoid.

On the distal ends 12 of the endoscope 10, optical devices are positioned in the shaft 14 that are not shown in FIG. 1. Said optical devices make possible a variation of the viewing angle of the endoscope between a first extreme viewing angle 21 and a second extreme viewing angle 22. The viewing angle can pivot between the two extreme viewing angles 21, 22 around a pivot axis 28, which is perpendicular to the plane of projection of FIG. 1. The viewing angle in each case is the angle based on the distal end 12 of the endoscope 10 in which an object is situated that appears in the center of an image recorded by means of the endoscope 10.

In the example shown in FIG. 1, the first extreme viewing angle 21 is parallel or essentially parallel to the longitudinal axis 18 of the endoscope 10. Between the extreme viewing angles 21, 22 lies an angle area 29 that is equal to approximately 120 degrees in the illustrated example. Within this angle area the viewing angle of the endoscope 10 is, in particular, continually adjustable or selectable.

On the proximal end 11 the endoscope 10 comprises a first coupling 32 for optically coupling the endoscope 10 with a video camera or eyepiece as well as a second coupling 34 for coupling the endoscope 10 with a light source via a light conductor cable. Alternatively, the image can also be recorded distally by a camera chip. From the second coupling 34, one or more lightwave conductors 35 lead through the shaft 14 to the distal end 11 of the endoscope 10. Illuminating light generated from a light source can be transmitted to the distal end 11 of the endoscope 10 by a light conductor cable, the coupling 34 or the lightwave conductor or conductors 35. Devices to conduct the illuminating light onto an object observed by the endoscope 10 are presented with reference to FIGS. 2 through 6.

FIGS. 2 through 6 show schematic depictions of one variant each of an endoscope 10 as was described above with reference to FIG. 1. Each of FIGS. 2 through 6 shows just one segment of the distal end 11 of the endoscope 10. Shown in each case is a section along a plane perpendicular to the plane of projection of FIG. 1 and parallel to the pivot axis 28 of the viewing angle 21, 22. The illustrated sectional planes in particular intersect the lightwave conductor 35 or one of the lightwave conductors 35. In FIGS. 2 through 6, the wall of the shaft 14 is merely depicted in each case in strongly simplified form as an L-shaped line, in order to indicate a rough distinction between the internal space of the endoscope and its surroundings and the arrangement of the illustrated elements relative to the distal end 11 of the endoscope illustrated in each case. In each of FIGS. 2 through 6, the distal end 11 of the individually illustrated endoscope 10 is shown in a configuration for illuminating a visual field in the first extreme viewing angle.

In each of the embodiments shown in FIGS. 2 through 6, a fixed reflecting surface 42 and a pivotable reflecting surface 52 are foreseen. In the illustrated examples, both reflecting surfaces 42, 52 are shown curved in each case. The fixed reflecting surface 42, in particular, is neither translationally nor rotationally movable with respect to the shaft 14 of the endoscope 10. The pivotable reflecting surface 52 in each case can pivot or rotate around a pivot axis 58. The pivot axis 58 is, in particular, parallel to the pivot axis 28 of the viewing angle 21, 22 of the endoscope. The pivot axis 58 of the pivotable reflecting surface 52 can be identical to the pivot axis 28 of the viewing angle 21, 22. In each of FIGS. 2 through 6, the pivot axis 58 of the pivotable reflecting surface 52 is situated in the plane of projection.

Alternatively, the pivot axis 28 of the viewing angle 21, 22, the pivot axis 58 of the pivotable reflecting surface 52, and the pivotable reflecting surface 52 itself can pivot around the longitudinal axis 18 of the endoscope 10 or around an axis parallel or essentially parallel to it.

Figure 2:
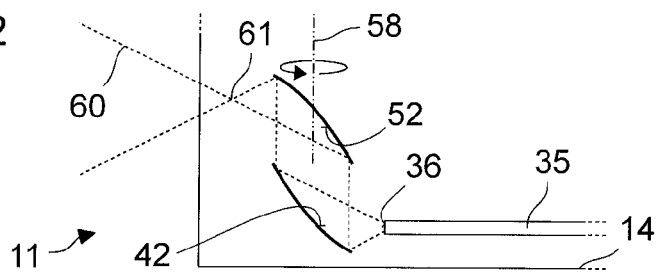
FIG. 2 shows a schematic depiction of a distal end of an endoscope with adjustable viewing angle.

FIG. 2 shows a schematic depiction of a distal end 11 of an embodiment of an endoscope, in which both reflecting surfaces 42, 52 are of concave configuration or have a gathering or bundling characteristic. The reflecting surfaces 42, 52 are, for example, reflecting surfaces or reflecting coatings of mirrors made of glass, plastic, ceramic or other material. Both the fixed reflecting surface 42 and the pivotable reflecting surface 52 have the shape of a segment of a paraboloid. The fixed reflecting surface 42, in particular, has the shape of a segment of a rotation paraboloid or of a rotation-symmetrical elliptical paraboloid at whose focal point a light outlet surface 36 of the lightwave conductor 35 is positioned.

Illuminating light transmitted by the lightwave conductor 35 exits at the light outlet surface 36. The angle area in which the illuminating light exits at the light outlet surface 36 is determined, on the basis of the transmission properties of the lightwave conductor 35, primarily by the properties of the coupling of the illuminating light on the proximal end of the lightwave conductor 35. The coupling of the illuminating light on the proximal end of the lightwave conductor 35 occurs by means of a transparent conical device, in particular a fiber cone or full cone. By means of this transparent cone, upon coupling of the illuminating light on the proximal end of the lightwave conductor 35, the diameter and divergence are selected at values suited for an optimal coupling. In particular, the properties of the transparent cone are selected in such a way that the greatest possible part of the provided illuminating light is coupled to the lightwave conductor 35 and transmitted by means of the lightwave conductor 35 to the distal end 11 of the endoscope 10.

The divergent illuminating light emanating from the light outlet surface 36 of the lightwave conductor 35 is collimated by the fixed reflecting surface 42 because the light outlet surface 36 is positioned at the focal point of the parabolic surface 42.

Downstream in the light path from the fixed reflecting surface 42, the illuminating light therefore runs parallel or essentially parallel to the axis of symmetry of the rotation paraboloid. The axis of symmetry of the rotation paraboloid is parallel to the pivot axis 58 of the pivotable reflecting surface 52. Thus the illuminating light propagates between the fixed reflecting surface 42 and the pivotable reflecting surface 52 parallel or essentially parallel to the pivot axis 58 of the pivotable reflecting surface 52.

The illuminating light reflected by the fixed reflecting surface 42 is then reflected by the pivotable reflecting surface 52. Because of the concave curvature of the pivotable reflecting surface 52, the illuminating light cone emitting from the pivotable reflecting surface 52 has a tapering 61 that is shown in idealized manner in FIG. 2. The opening angle of the illuminating light cone 60 is adjusted to the visual field of the endoscope. If the visual field of the endoscope is circular or rectangular, the pivotable reflecting surface 52 has, for example, the shape of a segment of a rotation paraboloid whose axis of symmetry is parallel to the pivot axis 58 of the pivotable reflecting surface 52. In this case the illuminating light cone 60 comprises the tapering 61 at the same location both in the sectional plane illustrated in FIG. 2 and in a section along a plane perpendicular to the plane of projection of FIG. 2 (parallel to the plane of projection of FIG. 1). The illuminating light cone 60 is thus rotation-symmetrical or essentially rotation-symmetrical to an axis of symmetry through the tapering 61.

Alternatively the pivotable reflecting surface 52 has, for example, the shape of a non-rotation-symmetrical elliptical paraboloid or a torical shape. In this case the illuminating light cone 60 emitting from the pivotable reflecting surface 52 can comprise taperings 61 at two different locations and accordingly can have two different opening angles in the sectional plane shown in FIG. 2 and in a sectional plane perpendicular to it. The illuminating light cone 60 in this way can be adjusted to a visual field with an aspect ratio that is not equal to 1:1.

The beam formation of the illuminating light or the shape of the illuminating light cone 60 and of the angle area illuminated by it as well as the distribution of intensity inside the illuminating light cone can be freely selected within broad boundaries by the fixed reflecting surface 42 and in particular by the pivotable reflecting surface 52. The size and curvature of the fixed reflecting surface 42 can be essentially adjusted to any desired radiant characteristic or to any desired intensity distribution of the illuminating light emitting from the light outlet surface 36 of the lightwave conductor 35. The coupling of the illuminating light on the proximal end of the lightwave conductor 35 is thus largely or completely independent of the angle area that is to be illuminated. The coupling of the illuminating light to the lightwave conductor 35 can therefore—for example, by means of the aforementioned transparent cone—be adjusted largely freely to an optimal coupling or to a transmission of a maximum radiant capacity by means of the lightwave conductor 35.

Figure 3:
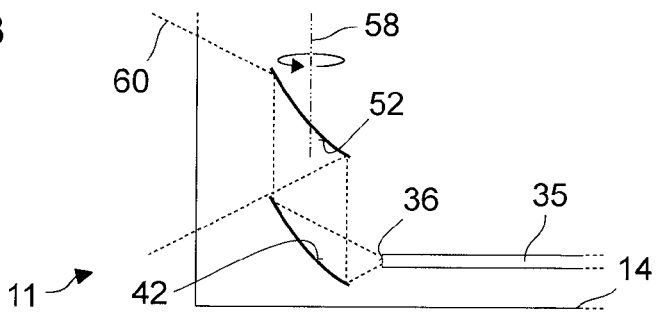
FIG. 3 shows a schematic depiction of a distal end of an additional endoscope with adjustable viewing angle.

FIG. 3 shows a schematic depiction of a distal end 11 of an embodiment of an endoscope that resembles in some aspects the embodiment presented above with reference to FIG. 2. The embodiment in FIG. 3 is distinguished from the embodiment presented above with reference to FIG. 2, in particular, in that the pivotable reflecting surface 52 is of convex, not concave, configuration. The illuminating light cone 60 emitting from the pivotable reflecting surface 52 therefore comprises, contrary to the embodiment presented above with reference to FIG. 2, no tapering 61. Similarly as in the embodiment presented above with reference to FIG. 2, it is possible also in the embodiment in FIG. 3 to adjust the illuminating light cone 60 largely to the visual field, in particular the size and aspect ratio of the visual field, by the curvature of the pivotable reflecting surface 52.

Also in the embodiment in FIG. 3, the pivotable reflecting surface 52 can have the shape of a rotation paraboloid whose axis of symmetry is parallel to the pivotable axis 58 of the pivotable reflecting surface 52. This shape of the pivotable reflecting surface 52 can be particularly suited for illuminating a visual field with an aspect ratio of 1:1. The illuminating light cone 60 can be adjusted to a visual field with a different aspect ratio by means of a different curvature of the pivotable reflecting surface 52. In particular, the pivotable reflecting surface 52 can have the shape of a segment of a non-rotation-symmetrical elliptical paraboloid or of a hyperbolic paraboloid or a torical shape. To illuminate a visual field whose aspect ratio departs from 1:1, the pivotable reflecting surface 52, in particular, has different strong curvatures in two sectional planes that are perpendicular to one another.

In each of the embodiments presented above with reference to FIGS. 2 and 3, both the fixed reflecting surface 42 and the pivotable reflecting surface 52, each departing from the illustrations in FIGS. 2 and 3, can be positioned on a transparent body inside which the illuminating light is partly propagated.

Figure 4:
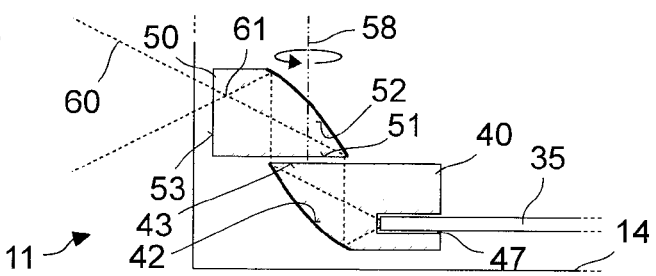
FIG. 4 shows a schematic depiction of a distal end of an additional endoscope with adjustable viewing angle.

FIG. 4 shows a schematic depiction of the distal end 11 of an embodiment of an endoscope that resembles in a few characteristics the embodiment presented above with reference to FIG. 2. However, contrary to the embodiment presented above with reference to FIG. 2, in the embodiment in FIG. 4 both the fixed reflecting surface 42 and the pivotable reflecting surface 52 are positioned or configured on a transparent body 40 or 50.

The distal end and the light outlet surface of the lightwave conductor 35, which is shown in FIG. 4 without a reference number for the sake of clarity, are joined with a fixed transparent body 40, in particular by means of a transparent cement. In particular, the distal end of the lightwave conductor 35 is positioned in a blind hole 47 in the fixed transparent body 40.

The pivotable reflecting surface 52 is positioned on a pivotable transparent body 50, which can pivot with the pivotable reflecting surface 52 around the pivot axis 58. A light outlet surface 43 of the fixed transparent body 40 is positioned opposite a light inlet surface 51 of the pivotable transparent body 50. The light outlet surface 43 of the fixed transparent body 40 and the light inlet surface 51 of the pivotable transparent body 50 in the illustrated example are each positioned flat and parallel to one another. Departing from the depiction in FIG. 4, both the light outlet surface 43 of the fixed transparent body 40 and the light inlet surface 51 of the pivotable transparent body 50 can be of convex or concave curvature.

The illuminating light reflected by the pivotable reflecting surface 52 of the pivotable transparent body 50 exits at a light outlet surface 53 of the pivotable transparent body 50 from said body. In the illustrated example the light outlet surface 53 of the pivotable transparent body 50 is flat. Contrary to the example illustrated in FIG. 4, the light outlet surface 53 of the pivotable transparent body 50 can be of convex or concave curvature.

Inside the fixed transparent body 50 and inside the pivotable transparent body 50, the illuminating light is propagated in a manner very similar to the example presented above with reference to FIG. 2. Because the illuminating light is propagated parallel to the pivot axis 58 of the pivotable transparent body 50 between the fixed reflecting surface 42 and the pivotable reflecting surface 52, the light outlet surface 43 of the fixed transparent body 40 and the light inlet surface 51 of the pivotable transparent body 50 have no effect on the propagation direction of the illuminating light if—as indicated in FIG. 4—they are flat and perpendicular to the pivot axis 58 of the pivotable transparent body 50.

The refraction of the illuminating light at the light outlet surface 53 of the pivotable transparent body 50 is not shown in FIG. 4. The refraction at the light outlet surface 53 of the pivotable transparent body 50 then has, for example, no impact or only a minor impact on the illuminating light cone 60 if and to the extent that it, contrary to the depiction in FIG. 4, is configured as spherical with a curvature center point at the tapering 61.

The arrangement of the distal end of the lightwave conductor 35 in a borehole in the fixed transparent body 40 allows a reliable mechanical connection. Alternatively the light outlet surface 36 of the lightwave conductor 35, contrary to the depiction in FIG. 4, can be joined in blunt-ended manner to a flat or curved light inlet surface of the fixed transparent body 40.

Contrary to the depiction in FIG. 4, the pivotable reflecting surface 52 can be configured on the pivotable transparent body 50, in similar manner as in the embodiment presented above with reference to FIG. 3, convex to the illuminating light that propagates in the pivotable transparent body 50. According to the usual meaning of the categorization of convex or concave for a surface of a body, the pivotable transparent body 50 in the area of the pivotable reflecting surface 52 would be concave. Examples that are of pivotable transparent configuration in this manner are described hereinafter with reference to FIGS. 5 and 6. The embodiments in FIGS. 5 and 6 are distinguished further from the embodiments described above with reference to FIGS. 2 through 4 in additional characteristics, particularly in the configuration of the fixed reflecting surface 42 and of the light outlet surface from which illuminating light emanates.

FIG. 5 shows a schematic depiction of the distal end of an additional embodiment of an endoscope. As previously mentioned, the pivotable transparent body 50 in the area of the pivotable reflecting surface 52 is arched inward, or concave. Based on the propagation of illuminating light inside the pivotable transparent body 50, the pivotable reflecting surface 52 is convex. The illuminating light that impinges essentially parallel on the pivotable reflecting surface 52 is reflected by the pivotable reflecting surface 52 in a divergent illuminating light cone that comprises no tapering. The effect of the pivotable reflecting surface 52 resembles in this respect the embodiment presented above with reference to FIG. 3. The refraction of the illuminating light at the light outlet surface 53 of the pivotable transparent body 50 is not shown in FIG. 5.

The embodiment in FIG. 5 is distinguished from the embodiments described above with reference to FIGS. 2 through 4 in that the fixed reflecting surface 42 is configured on a rotation-symmetrical parabolic part of the surface of a fixed transparent body 40.

The embodiment in FIG. 5 is further distinguished from the embodiments described above and shown in FIGS. 2 through 4 in that a photoluminescent body 37 is positioned in the focal point of the rotation-symmetrical parabolic fixed reflecting surface 42. The photoluminescent body 37, in particular, is positioned on the distal end of the lightwave conductor 35 in a blind hole 47 in the fixed transparent body 40. The photoluminescent body 37, in particular, comprises a fluorescent or phosphorescent material, which, upon excitation by means of excitation light of a laser or other light source, emits fluorescent or phosphorescent light via the lightwave conductor 35. The material of the photoluminescent body 37 is selected in particular in such a way that the spectrum of the fluorescent or phosphorescent light, possibly together with the spectrum of excitation light that is scattered by the photoluminescent body 37, appears white.

For low-loss coupling of excitation light transmitted by means of the lightwave conductor 35 to the photoluminescent body 37 and of fluorescent or phosphorescent light from the photoluminescent body 37 to the fixed transparent body 40, the lightwave conductor 35 and the photoluminescent body 37 and/or the photoluminescent body 37 and the fixed transparent body 40 are joined, in particular by means of a transparent cement with appropriate refractive index.

The surface of the photoluminescent body 37 constitutes a light outlet surface from which fluorescent or phosphorescent light is emitted essentially in all directions. On the basis of the arrangement of the photoluminescent body 37 in the focal point of the rotation paraboloid of the fixed reflecting surface 42, the illuminating light reflected by the fixed reflecting surface 42 is propagated essentially parallel to the pivot axis 58 of the pivotable transparent body 50.

FIG. 6 shows a schematic depiction of the distal end of an additional embodiment of an endoscope, which resembles in some respects the embodiment presented above and shown in FIG. 5. The embodiment in FIG. 6 differs from the embodiment presented above with reference to FIG. 5, in particular, in that no lightwave conductor 35 is foreseen and in that, instead of a photoluminescent body, a luminescent body 39, for example an organic or inorganic light-emitting diode, is positioned. The surface 36 of the luminescent body 39 is a light outlet surface through which the illuminating light exits.

The embodiment in FIG. 6 further differs from the embodiment presented above with reference to FIG. 5 in that no fixed transparent body is foreseen. The fixed reflecting surface 42 thus is not a surface of a fixed transparent body but rather, for example, the reflecting surface of a mirror. The propagation of the illuminating light emanating from the luminescent body 39 resembles the propagation of the illuminating light in the embodiment described above with reference to FIG. 5.

Photoluminescent or luminescent bodies 37, 39 and fixed reflecting surfaces 42, as foreseen in the embodiments presented above and shown in FIGS. 5 and 6, can also be used in the embodiments presented above and shown in FIGS. 2 through 4. In addition, also in the embodiments presented above with reference to FIGS. 5 and 6, pivotable reflecting surfaces 52 or pivotable transparent bodies 50 as were presented above with reference to FIGS. 2 through 4 can each be used.

Figure 7:
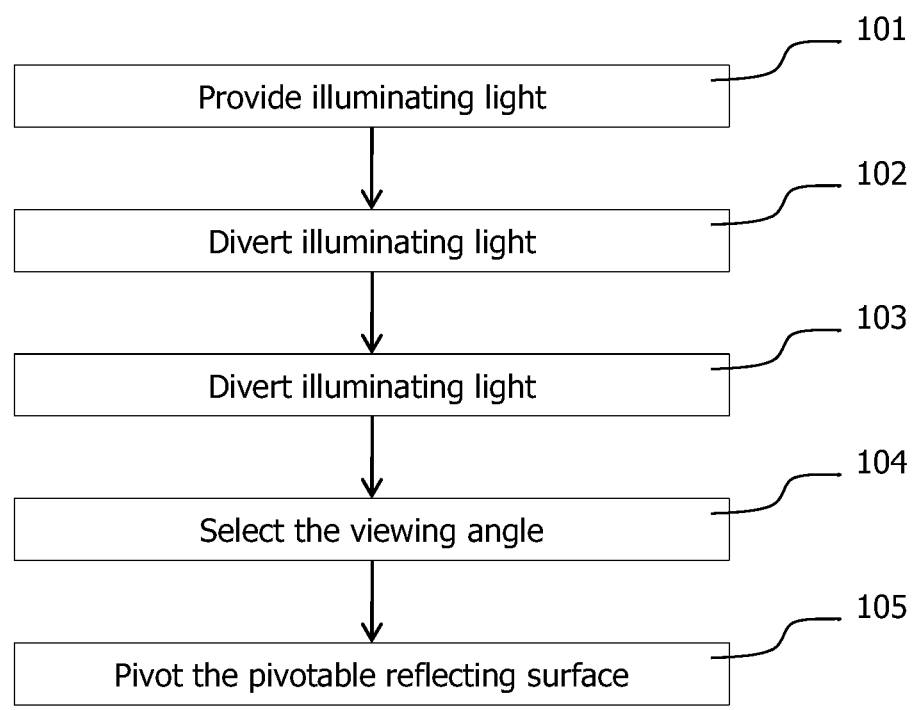
FIG. 7 shows a schematic flow diagram.

FIG. 7 shows a schematic flow diagram for a method for illuminating a visual field in a viewing angle of an endoscope, such that the viewing angle of the endoscope can pivot around a pivot axis. Although the method can also be executed with an endoscope that differs from the embodiments presented above with reference to FIGS. 1 through 6, in the following presentation reference numbers from FIGS. 1 through 6 are used in exemplary manner for the sake of clarity.

In a first step 101, illuminating light is provided. This occurs, for example, by means of a light-emitting diode or other luminescent body 39 on the distal end 11 or on the proximal end 12 of the endoscope 10, by a body 37 that is in particular fluorescent and/or phosphorescent and is excited to photoluminescence or by another light source positioned on the distal end 11 or on the proximal end 12 of the endoscope 10 or outside the endoscope 10. The illuminating light generated by the light source can be conducted to the distal end 11 of the endoscope 10 by means of a lightwave conductor 35.

In a second step 102, the illuminating light provided in the first step 101 is diverted to a direction parallel to the pivot axis 28 of the viewing angle 21, 22 by means of a fixed reflecting surface 42. The illuminating light here is simultaneously collimated, in particular because of a curvature of the fixed reflecting surface 42.

In a third step 103, the illuminating light diverted by means of the fixed reflecting surface 42 is diverted into the momentarily selected viewing angle by means of a pivotable reflecting surface 52. In particular, the illuminating light here is directed not only into the momentarily selected viewing angle but also into an angle space around the momentarily selected viewing angle that corresponds to the visual field for the momentarily selected viewing angle. The area or angle area radiated or illuminated by the illuminating light is adjusted to the visual field for the momentarily selected viewing angle by a curvature of the fixed reflecting surface 42 and/or by a curvature of the pivotable reflecting surface 52. This occurs in particular as described above with reference to FIGS. 2 through 6.

In a fourth step 104, the viewing angle 21, 22 of the endoscope 10 is selected. In a fifth step 105, the pivotable reflecting surface 52 corresponding to the viewing angle 21, 22 selected in the fourth step 104 is pivoted. The fourth step 104 and fifth step 105 are, in particular, executed simultaneously. The fourth step 104 and fifth step 105 can be performed even before the first step 101.

What is claimed is:

1. An endoscope with adjustable viewing angle, such that the viewing angle can pivot around a pivot axis, with:
   a fixed reflecting surface to reflect illuminating light being transmitted in a distal direction from a light source from a direction parallel to a longitudinal axis of the endoscope to a direction parallel to the pivot axis of the viewing angle;
   a pivotable reflecting surface to reflect the illuminating light from the direction parallel to the pivot axis of the viewing angle to the viewing angle, the pivotable reflecting surface providing a field of illumination out of the endoscope to illuminate an object to be observed by the endoscope,
   such that at least one of the fixed reflecting surface or the pivotable reflecting surface is curved;
   wherein the pivotable reflecting surface has a curvature which configures the field of illumination with a width-to-height ratio corresponding to a width-to-height ratio of a visual field of the viewing angle.

2. The endoscope according to claim 1, wherein the fixed reflecting surface is configured and positioned in order to collimate the illuminating light.

3. The endoscope according to claim 1, wherein the fixed reflecting surface has the shape of a segment of a paraboloid.

4. The endoscope according to claim 3, wherein a light outlet surface of a lightwave conductor or of a light source is positioned at a focal point of the paraboloid.

5. The endoscope according to claim 1, wherein the pivotable reflecting surface has the shape of a segment of a paraboloid or is of torical shape.

6. The endoscope according to claim 1, wherein at least either the fixed reflecting surface or the pivotable reflecting surface is positioned on a transparent body.

7. The endoscope according to claim 1, wherein the fixed reflecting surface is positioned on a transparent body, such that the transparent body and a light outlet surface of a lightwave conductor or of a light source are joined by means of a transparent cement.

8. The endoscope according to claim 1, wherein the pivotable reflecting surface and the fixed reflecting surface are configured and positioned in such a way that a light bundle of illuminating light exiting on a distal end of the endoscope comprises a tapering downstream in the light path from the pivotable reflecting surface.

9. A method for illuminating a visual field in a viewing angle of an endoscope, such that the viewing angle of the endoscope can pivot around a pivot axis, with the following steps:
   provide illuminating light from a light source;
   divert the provided illuminating light being transmitted in a distal direction at first by means of a fixed reflecting surface to a direction parallel to the pivot axis and then by means of a pivotable reflecting surface to the momentarily selected viewing angle, the pivotable reflecting surface providing a field of illumination out of the endoscope,
   such that an area irradiated by the illuminating light is adjusted to the visual field upon diversion by at least one of a curvature of the fixed reflecting surface or a curvature of the pivotable reflecting surface, wherein the pivotable reflecting surface has a curvature which configures the field of illumination with a width-to-height ratio corresponding to a width-to-height ratio of the visual field.

* * * * *